(12) United States Patent
Ladet et al.

(10) Patent No.: US 8,663,689 B2
(45) Date of Patent: Mar. 4, 2014

(54) FUNCTIONALIZED ADHESIVE MEDICAL GEL

(75) Inventors: Sebastien Ladet, Lyons (FR); Philippe Gravagna, Irigny (FR)

(73) Assignee: Sofradim Production (FR)

( * ) Notice: Subject to any disclaimer, the term of this patent is extended or adjusted under 35 U.S.C. 154(b) by 523 days.

(21) Appl. No.: 12/708,828

(22) Filed: Feb. 19, 2010

(65) Prior Publication Data

US 2010/0215748 A1 Aug. 26, 2010

Related U.S. Application Data

(60) Provisional application No. 61/154,369, filed on Feb. 21, 2009.

(51) Int. Cl.
*A61K 9/14* (2006.01)

(52) U.S. Cl.
USPC .......................................................... 424/487

(58) Field of Classification Search
USPC .......................................................... 424/487
See application file for complete search history.

(56) References Cited

U.S. PATENT DOCUMENTS

| | | | |
|---|---|---|---|
| 3,767,085 A | 10/1973 | Cannon et al. |
| 4,359,049 A | 11/1982 | Redl et al. |
| 4,361,055 A | 11/1982 | Kinson |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,874,368 A | 10/1989 | Miller et al. |
| 4,880,662 A | 11/1989 | Habrich et al. |
| 4,978,336 A | 12/1990 | Capozzi et al. |
| 4,979,942 A | 12/1990 | Wolf et al. |
| 5,368,563 A | 11/1994 | Lonneman et al. |
| 5,372,585 A | 12/1994 | Tiefenbrun et al. |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,911,942 A | 6/1999 | Fofonoff et al. |
| 6,107,365 A | 8/2000 | Bertozzi et al. |
| 6,107,453 A | 8/2000 | Zuccato et al. |
| 6,451,032 B1 | 9/2002 | Ory et al. |
| 6,527,749 B1 | 3/2003 | Roby et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,881,766 B2 | 4/2005 | Hain |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,667,012 B2 | 2/2010 | Saxon et al. |
| 8,034,396 B2 * | 10/2011 | Kapiamba et al. ........... 427/2.13 |
| 2002/0016003 A1 | 2/2002 | Saxon et al. |
| 2002/0161170 A1 | 10/2002 | Matsuda et al. |
| 2002/0169275 A1 | 11/2002 | Matsuda et al. |
| 2002/0173616 A1 | 11/2002 | Matsuda et al. |
| 2003/0100086 A1 | 5/2003 | Yao et al. |
| 2003/0135238 A1 | 7/2003 | Milbocker |
| 2003/0199084 A1 | 10/2003 | Saxon et al. |
| 2003/0205454 A1 | 11/2003 | Hlavinka et al. |
| 2004/0170752 A1 | 9/2004 | Luthra et al. |

(Continued)

FOREIGN PATENT DOCUMENTS

| | | | |
|---|---|---|---|
| EP | 0077098 A2 | 4/1983 |
| EP | 0328050 A2 | 8/1989 |

(Continued)

OTHER PUBLICATIONS

Wang et al (Multifunctional chondroitin sulphate for cartilage tissue-biomaterial integration. Nat Mater. May 2007;6(5):385-92. Epub Apr. 15, 2007).*

Crescenzi et al (Novel hydrogels via click chemistry: synthesis and potential biomedical applications. Biomacromolecules. Jun. 2007;8(6):1844-50. Epub May 25, 2007).*

Q. Shi, et al., "The Immobilization of Proteins on Biodegradeable Polymer Fibers via Click Chemistry", Biomaterials, 29, (2008), pp. 1118-1126.

Jérôme, et al., "Recent Advances in the Synthesis of Aliphatic Polyesters Ring-Opening Polymerization", Advanced Drug Delivery Reviews, 60, (2008), pp. 1056-1076.

Zhang, et al., "2-Azido-2-deoxycellulose: Synthesis and 1, 3-Dipolar Cycloaddition", Helvetica Chimica Acta, vol. 91, pp. 608-617 (2008).

(Continued)

*Primary Examiner* — Jake Vu

(74) *Attorney, Agent, or Firm* — Carter, DeLuca, Farrell & Schmidt, LLP

(57) ABSTRACT

A bioadherent substrate includes a medical gel or medical gel precursor having a plurality of reactive members of a specific binding pair attached on or adapted to be attached to a surface of the medical gel, said reactive members being capable of forming covalent bonds with a plurality of complementary reactive members of the specific binding pair via a reaction selected from a Huisgen cycloaddition reaction, a Diels-Alder reaction and a thiol-ene reaction. A method for adhering a medical gel to biological tissue includes providing a medical gel or a medical gel precursor having a plurality of reactive members of a specific binding pair attached on or adapted to be attached to a surface of the medical gel and providing tissue with a plurality of complementary reactive members of the specific binding pair, wherein upon contact of the reactive members on the medical gel with the complimentary reactive members on the tissue, covalent bonds are formed between the reactive members and the complementary reactive members, thus adhering the medical gel to the tissue.

11 Claims, No Drawings

(56) References Cited

U.S. PATENT DOCUMENTS

| | | |
|---|---|---|
| 2004/0185053 A1 | 9/2004 | Govindan |
| 2004/0209317 A1 | 10/2004 | Ting |
| 2005/0038472 A1 | 2/2005 | Furst |
| 2005/0148032 A1 | 7/2005 | Saxon et al. |
| 2005/0222427 A1 | 10/2005 | Sharpless et al. |
| 2005/0233389 A1 | 10/2005 | Ting et al. |
| 2006/0018948 A1 | 1/2006 | Guire et al. |
| 2006/0085033 A1 | 4/2006 | Criscuolo et al. |
| 2006/0108393 A1 | 5/2006 | Heinrich et al. |
| 2006/0110782 A1 | 5/2006 | Bertozzi et al. |
| 2006/0147963 A1 | 7/2006 | Barone et al. |
| 2006/0193865 A1 | 8/2006 | Govindan |
| 2006/0228300 A1 | 10/2006 | Chang et al. |
| 2006/0228357 A1 | 10/2006 | Chang et al. |
| 2006/0240092 A1 | 10/2006 | Breitenkamp et al. |
| 2006/0276658 A1 | 12/2006 | Saxon et al. |
| 2007/0020620 A1 | 1/2007 | Finn et al. |
| 2007/0037964 A1 | 2/2007 | Saxon et al. |
| 2007/0060658 A1 | 3/2007 | Diaz et al. |
| 2007/0077564 A1 | 4/2007 | Roitman et al. |
| 2007/0086942 A1 | 4/2007 | Chang et al. |
| 2007/0087001 A1 | 4/2007 | Taylor et al. |
| 2007/0099251 A1 | 5/2007 | Zhang et al. |
| 2007/0140966 A1 | 6/2007 | Chang et al. |
| 2007/0178133 A1 | 8/2007 | Rolland |
| 2007/0178448 A1 | 8/2007 | Tsao et al. |
| 2007/0190597 A1 | 8/2007 | Agnew et al. |
| 2007/0244265 A1 | 10/2007 | Matyjaszewski et al. |
| 2007/0244296 A1 | 10/2007 | Tomalia et al. |
| 2007/0249014 A1 | 10/2007 | Agnew et al. |
| 2007/0254006 A1 | 11/2007 | Loose et al. |
| 2007/0258889 A1 | 11/2007 | Douglas et al. |
| 2007/0269369 A1 | 11/2007 | Gegg et al. |
| 2007/0272122 A1 | 11/2007 | Lahann et al. |
| 2007/0275387 A1 | 11/2007 | Ju |
| 2007/0298006 A1 | 12/2007 | Tomalia et al. |
| 2008/0015138 A1 | 1/2008 | Hamilton et al. |
| 2008/0035243 A1 | 2/2008 | Breitenkamp et al. |
| 2008/0038472 A1 | 2/2008 | Suzuki et al. |
| 2008/0045686 A1 | 2/2008 | Meagher et al. |
| 2008/0050731 A1 | 2/2008 | Agnew et al. |
| 2008/0051562 A1 | 2/2008 | Chaikof et al. |
| 2008/0121657 A1 | 5/2008 | Voegele et al. |
| 2008/0138317 A1 | 6/2008 | Fung |
| 2008/0160017 A1 | 7/2008 | Baker et al. |
| 2008/0166363 A1 | 7/2008 | Govindan et al. |
| 2008/0171067 A1 | 7/2008 | Govindan et al. |
| 2008/0187956 A1 | 8/2008 | Carrico et al. |
| 2008/0199736 A1 | 8/2008 | Gadeken et al. |
| 2008/0200628 A1 | 8/2008 | Gadeken et al. |
| 2008/0207913 A1 | 8/2008 | Breitenkamp et al. |
| 2008/0214436 A1 | 9/2008 | Yu et al. |
| 2008/0214801 A1 | 9/2008 | Saxon et al. |
| 2008/0214831 A1 | 9/2008 | Sharpless et al. |
| 2008/0221043 A1 | 9/2008 | Harth et al. |
| 2008/0241856 A1 | 10/2008 | Wong et al. |
| 2008/0241892 A1 | 10/2008 | Roitman et al. |
| 2008/0242171 A1 | 10/2008 | Huang et al. |
| 2008/0248126 A1 | 10/2008 | Cheng et al. |
| 2008/0267878 A1 | 10/2008 | Robillard et al. |
| 2008/0283572 A1 | 11/2008 | Boyden et al. |
| 2008/0311412 A1 | 12/2008 | Fokin et al. |
| 2009/0012457 A1 | 1/2009 | Childers et al. |
| 2009/0018646 A1 | 1/2009 | Zhao |
| 2009/0053139 A1 | 2/2009 | Shi et al. |
| 2009/0054619 A1 | 2/2009 | Baker et al. |
| 2009/0061010 A1 | 3/2009 | Zale et al. |
| 2009/0069561 A1 | 3/2009 | Fokin et al. |
| 2009/0082224 A1 | 3/2009 | Haddleton et al. |
| 2009/0124534 A1 | 5/2009 | Reineke et al. |
| 2009/0137424 A1 | 5/2009 | Tsao et al. |
| 2009/0181402 A1 | 7/2009 | Finn et al. |
| 2009/0182151 A1 | 7/2009 | Wu et al. |
| 2009/0202433 A1 | 8/2009 | Chang et al. |
| 2009/0214755 A1 | 8/2009 | Armani et al. |
| 2009/0220607 A1 | 9/2009 | Kiser et al. |
| 2009/0240030 A1 | 9/2009 | Ju et al. |
| 2009/0247651 A1 | 10/2009 | Kapiamba et al. |
| 2009/0250588 A1 | 10/2009 | Robeson et al. |
| 2009/0253609 A1 | 10/2009 | Fleury et al. |
| 2009/0259016 A1 | 10/2009 | Johnson et al. |
| 2009/0263468 A1 | 10/2009 | McAnulty et al. |
| 2009/0269277 A1 | 10/2009 | Chang et al. |
| 2009/0281250 A1 | 11/2009 | DeSimone et al. |
| 2009/0297609 A1 | 12/2009 | Shoichet et al. |
| 2009/0306310 A1 | 12/2009 | Wu et al. |
| 2009/0312363 A1 | 12/2009 | Bradner et al. |
| 2010/0011472 A1 | 1/2010 | Hugel et al. |
| 2010/0015046 A1 | 1/2010 | Govindan et al. |
| 2010/0021391 A1 | 1/2010 | Douglas et al. |
| 2010/0034862 A1 | 2/2010 | Laronde et al. |
| 2010/0047258 A1 | 2/2010 | Wang et al. |
| 2010/0048738 A1 | 2/2010 | Fleury et al. |
| 2010/0069578 A1 | 3/2010 | Faust et al. |
| 2010/0098640 A1 | 4/2010 | Cohen et al. |
| 2010/0121022 A1 | 5/2010 | Musa et al. |
| 2010/0159011 A1 | 6/2010 | Lian et al. |

FOREIGN PATENT DOCUMENTS

| | | |
|---|---|---|
| EP | 0490854 B1 | 9/1996 |
| EP | 1975230 A1 | 1/2008 |
| EP | 2090592 A1 | 8/2009 |
| WO | WO 00/62827 | 10/2000 |
| WO | WO 2004/054622 A1 | 7/2004 |
| WO | WO 2005/062854 A2 | 7/2005 |
| WO | WO 2005/079217 A2 | 9/2005 |
| WO | WO 2005/084180 A2 | 9/2005 |
| WO | WO 2005/084367 A2 | 9/2005 |
| WO | WO 2005/087818 A1 | 9/2005 |
| WO | WO 2005/113605 A1 | 12/2005 |
| WO | WO 2006/005046 A2 | 1/2006 |
| WO | WO 2006/012569 A1 | 2/2006 |
| WO | WO 2006/050262 A2 | 5/2006 |
| WO | WO 2006/065266 A2 | 6/2006 |
| WO | WO 2006/084202 A2 | 8/2006 |
| WO | WO 2006/086325 A2 | 8/2006 |
| WO | WO 2006/091894 A2 | 8/2006 |
| WO | WO 2006/107617 A2 | 10/2006 |
| WO | WO 2006/107786 A2 | 10/2006 |
| WO | WO 2006/107903 A2 | 10/2006 |
| WO | WO 2007/003054 A1 | 1/2007 |
| WO | WO 2007/041394 A2 | 4/2007 |
| WO | WO 2007/041451 A2 | 4/2007 |
| WO | WO 2007/047668 A2 | 4/2007 |
| WO | WO 2008/004988 A1 | 1/2008 |
| WO | WO 2008/013618 A1 | 1/2008 |
| WO | WO 2008/031525 A1 | 3/2008 |
| WO | WO 2008/047057 A1 | 4/2008 |
| WO | WO 2008/075955 A2 | 6/2008 |
| WO | WO 2008/077406 A2 | 7/2008 |
| WO | WO 2008/108736 A1 | 9/2008 |
| WO | WO 2008/115694 A2 | 9/2008 |
| WO | WO 2008/120016 A1 | 10/2008 |
| WO | WO 2009/029242 A1 | 3/2009 |
| WO | WO 2009/064696 A1 | 5/2009 |
| WO | WO 2009/136853 A1 | 11/2009 |
| WO | WO 2009/140429 A2 | 11/2009 |

OTHER PUBLICATIONS

R. Riva, et al., "Contribution of "Click Chemisty" to the Synthesis of Antimicrobial Aliphatic Copolyester", Polymer 49, (2008), pp. 2023-2028.

Baskin, et al., "Copper Free Click Chemistry for Dynamic In Vivo Imaging", PNAS, vol. 104, No. 43, (Oct. 23, 2007), pp. 16793-16797.

Codelli, et al., "Second Generation Difluorinated Cyclooctynes for Copper-Free Click Chemistry", J. Am. Chem. Soc., vol. 130, No. 34, (2008), pp. 11486-11493.

Sletton and Bertozzi, "A Hydrophilic Azacyclooctyne for Cu-free Click Chemistry", Org. Lett. (2008) 10(14), pp. 3097-3099.

Cazalis, et al., "Bioconjugate Chem.", 15 (2004), pp. 1005-1009.

(56) References Cited

OTHER PUBLICATIONS

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDevedec, et al., "Separation of Chitosan Oligomers by Immobilized Metal Affinity Chromatography", J. Chromatogr A., 2008, 1194(2), pp. 165-171.

Hartgerink, et al., "Pepti-damphiphile Nanofibers: A Versatile Scaffold for the Preparation of Self Assembling Materials", PNAS, 2002; 99(2), pp. 5133-5138.

Van Berkel, et al., Cem Bio Chem, 8, (2007), pp. 1504-1508.

Nottelet, et al., Biomaterials, 27, (2006), pp. 4948-4954.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-*O*-acetyl-1-thio-β-D-glucopyranose to 4-deoxy-1,2-*O*-isopropylident-L-*glycero*-pent-4-enopyranos-3-ulose-a convenient route to novel 4-deoxy-(1→5)-5-*C*-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel Domino-click Approach for the Synthesis of Sugar Based Unsymmetrical bis-1,2,3-triazoles", Carbohydrate Research, 343, (2008), 139-144.

Chen, et al., "Synthesis of a $C_3$-symmetric (1→6)-N-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, et al., "Effects of Trehalose Click Polymer Length on pDNA Complex Stability and Delivery Efficacy", Biomaterials, 28, (2007), pp. 2885-2898.

Godeau, et al., "Lipid-Conjugated Oligonucleotides via Click Chemistry" Efficiently Inhibit Hepatitis C Virus Translation, J. med. Chem., 2008, 51(15), pp. 4374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i* + 4 Intramolecular Side-chain to Side-chain Azide-Alkyne 1,3-Dipolar Cycloaddition" J. Org. Chem., 2008, 73 (15), pp. 5663-5674.

Dijk, et al., Synthesis of Peptide-Based Polymers by Microwave-Assisted Cycloaddition Backbone Polymerization, Biomacro molecules, 2007, 8(2), pp. 327-330.

Köster, et al., "Spectroscopic and Electrochemical Studies of Ferroceryl Triazole Amino Acid and Peptide Bioconjugates Synthesized by Click Chemisty", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradeable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Crescenzi, et al., "Novel Hydrogels via Click Chemistry: Synthesis and Potential Biomedical Applications", Biomacromolecules, Jun. 1, 2007, vol. 8, No. 6, pp. 1844-1850.

Wang, et al., "Multifunctional Chondroitin Sulphate for Cartilage Tissue Biomaterial Integration", Nature Materials, Nature Publishing Group, Jan. 1, 2007, vol. 6, pp. 385-392.

Diaz, et al., "Click Chemistry in materials Synthesis. 1, Adhesive Polymers from Copper-Catalyzed Azide-Alkyne Cycloaddition", Journal of Polymer Chemistry, Jan. 1, 2004, vol. 42, No. 17, pp. 4392-4403.

European Search Report corresponding to European Application No. 13156082.3-1455; completed on Jun. 20, 2012 and mailed Jun. 28, 2013; (5 Pages).

* cited by examiner

FUNCTIONALIZED ADHESIVE MEDICAL GEL

RELATED APPLICATIONS

This application claims the benefit of U.S. Provisional Patent Application No. 61/154,369 filed Feb. 21, 2009.

BACKGROUND

1. Technical Field

The present disclosure relates to adhesive modalities for repair of biological tissues.

2. Related Art

Medical adhesives or "tissue glue" have much potential in medicine. Certain adhesive materials are known which may be used to adhere tissue such as skin. For example, cyanoacrylate adhesives been used to bond tissue. In addition to cyanoacrylate adhesives, other types of materials have been reported to adhere to skin. For example, U.S. Pat. No. 4,839,345 to Doi et al. reports a hydrated crosslinked protein adhesive gel that is used as a cataplasm or cosmetic mask that will externally adhere to skin but can be removed and then re-adhered to the skin. Other crosslinked protein hydrogels have been reported to serve as a proteinaceous substrate to deliver therapeutic agents such as enzymes or drugs through skin or mucous membranes. Still other materials have been used as hemostatic agents to stop or prevent bleeding. For example, mixtures of fibrinogen and thrombin such as TISSEEL® sealant available from Baxter International, Inc. or BERIPLAST-P® hemostatic agent or sealant available from Aventis Behring, have been used in vascular surgery to seal tissue such as blood vessels and thus prevent blood leakage. However, surgical adhesives can tend to form a physical barrier between the item or items being attached to biological tissue, thus interfering with tissue ingrowth into the item when ingrowth is desired.

The use of medical gels such as hydrogels can be advantageous due to the physico-chemical properties of the hydrogels. Hydrogels typically have excellent compatibility with human and animal tissue. Physically cross linked hydrogels can withstand attack by body fluids, blood, urine and other bodily secretions without significant damage. Many are typically non-adherent to tissue, do not have an affinity for binding to proteins and do not have cell adsorption. Hydrogels are typically non-thrombogenic. These characteristics have been utilized, e.g., for prevention of adhesions after surgery. The ability of hydrogels to act as bulking agents has been utilized in connection with treatment of gastroesophageal reflux disease (GERD), urinary incontinence, fecal incontinence and sterilization of mammals. Hydrogels have also been used to create a matrix in the treatment of damaged cartilage.

Click chemistry is a popular term for reliable reactions that make it possible for certain chemical building blocks to "click" together and form an irreversible linkage. See, e.g., US Pub. No. 2005/0222427. In the case of azide-alkyne click chemistry, the reactions may be catalyzed or uncatalyzed. For example, copper-free click chemistry was recently developed by Bertozzi and colleagues using difluorinated cyclooctyne or DIFO, that reacts with azides rapidly at physiological temperatures without the need for a toxic catalyst. See, e.g., Baskin et al., Copper Free Click Chemistry for Dynamic In Vivo Imaging, PNAS, vol. 104, no. 43, 16793-16797 (Oct. 23, 2007). The critical reagent, a substituted cyclooctyne, possesses ring strain and electron-withdrawing fluorine substituents that together promote a [3+2] dipolar cycloaddition with azides. See also, US Pub. No. 2006/0110782 and Codelli et al., Second Generation Difluorinated Cyclooctynes for Copper-Free Click Chemistry, J. Am. Chem. Soc., vol. 130, no. 34, 11486-11493 (2008). Another suitable cyclooctyne is 6,7-dimethoxyazacyclooct-4-yne (DIMAC). See, Sletton and Bertozzi, A hydrophilic azacyclooctyne for Cu-free click chemistry, Org. Lett. (2008) 10 (14), 3097-3099. Other click chemistry reactions include Diels-Alder reactions, thiol-alkene reactions, and maleimide-thiol reactions.

It would be advantageous to be able to secure medical gels via selective attachment at target sites within the body to prevent migration of the hydrogel without interfering with other hydrogel properties such as durability and the ability to be generally non-adherent when or where desired.

SUMMARY

A method for adhering a medical gel to biological tissue is provided which includes providing a medical gel having a plurality of reactive members of a specific binding pair attached on to a medical gel or to precursor molecules of the medical gel, and providing tissue with a plurality of complementary reactive members of the specific binding pair, wherein upon contact of the reactive members of the medical gel with the complimentary reactive members on the tissue, covalent bonds are formed between the reactive members and the complementary reactive members, thus adhering the medical gel to the tissue.

A bioadherent substrate is provided which includes a medical gel having a plurality of reactive members of a specific binding pair attached thereto, said reactive members being capable of forming covalent bonds with a plurality of complementary reactive members of the specific binding pair via a reaction selected from a Huisgen cycloaddition, a Diels-Alder reaction, a thiol-alkene reaction.

A kit is provided which includes a functionalized medical gel or medical gel precursor molecules having a plurality of reactive members of a specific binding pair adapted to be attached to the gel or medical gel precursor molecules; a container containing a solution or suspension of complementary reactive members of the specific binding pair, the complementary reactive members having a functionality that will adhere them to biological tissue upon contact; and at least one applicator adapted to deliver the functionalized medical gel or medical gel precursors or the solution or suspension to biological tissue.

DETAILED DESCRIPTION

A surgical adhesive system for medical gels and biological tissue is provided which covalently bonds reactive members of a specific binding pair to one another via click chemistry. Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

Huisgen cycloaddition is the reaction of a dipolarophile with a 1,3-dipolar compound that leads to 5-membered (hetero)cycles. Examples of dipolarophiles are alkenes and alkynes and molecules that possess related heteroatom functional groups (such as carbonyls and nitriles). 1,3-Dipolar compounds contain one or more heteroatoms and can be described as having at least one mesomeric structure that represents a charged dipole. They include nitril oxides, azides, and diazoalkanes. Metal catalyzed click chemistry is an extremely efficient variant of the Huisgen 1,3-dipolar cycloaddition reaction between alkyl-aryly-sulfonyl azides, C—N triple bonds and C—C triple bonds which is well-suited herein. The results of these reactions are 1,2 oxazoles, 1,2,3 triazoles or tetrazoles. For example, 1,2,3 triazoles are formed by a copper catalyzed Huisgen reaction between alkynes and alkyl/aryl azides. Metal catalyzed Huisgen reactions proceed at ambient temperature, are not sensitive to solvents, i.e., nonpolar, polar, semipolar, and are highly tolerant of functional groups. Non-metal Huisgen reactions (also referred to as strain promoted cycloaddition) involving use of a substituted cyclooctyne, which possesses ring strain and electron-withdrawing substituents such as fluorine, that together promote a [3+2] dipolar cycloaddition with azides are especially well-suited for use herein due to low toxicity as compared to the metal catalyzed reactions. Examples include DIFO and DIMAC. Reaction of the alkynes and azides is very specific and essentially inert against the chemical environment of biological tissues. One reaction scheme may be represented as:

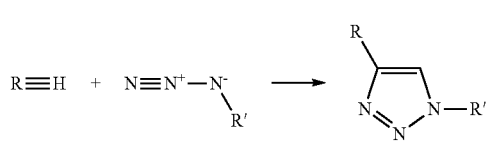

a)

where R is a polymeric backbone and R' is a component of a biologic tissue. Alternatively, R is a component of a biologic tissue and R' is a polymeric backbone.

The Diels-Alder reaction combines a diene (a molecule with two alternating double bonds) and a dienophile (an alkene) to make rings and bicyclic compounds. Examples include:

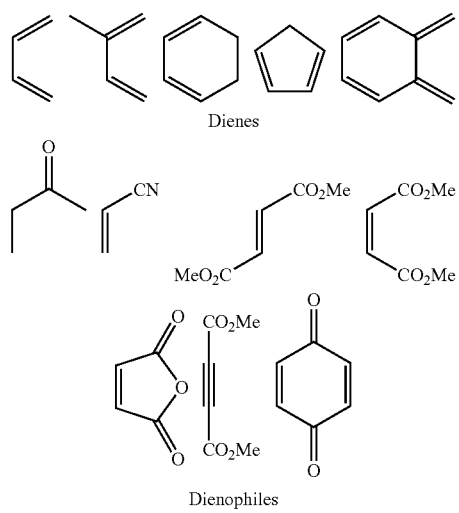

The thiol-alkene (thiol-ene) reaction is a hydrothiolation, i.e., addition of RS—H across a C═C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

Initiation

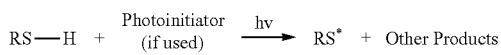

Propagation

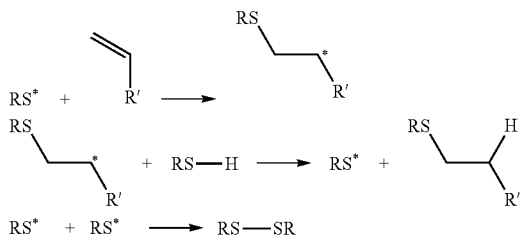

Termination

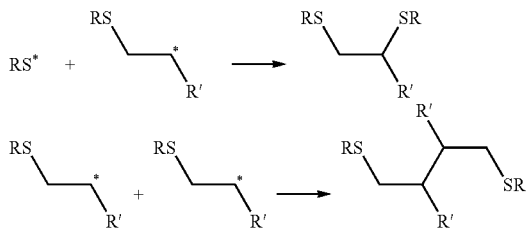

In accordance with the disclosure herein, a medical gel, such as a hydrogel, is provided with a plurality of reactive members of a specific binding pair attached on the surface of the gel or to precursor molecules which form the gel. As used herein, unless otherwise specified, "attached to the surface of the gel" or "attached on the surface of the gel" or "located on the gel" is intended to include attachment to molecules which are precursors of the gel. When the reactive members of the medical gel are contacted with biological tissue containing complementary reactive members of the specific binding pair, covalent attachment occurs, thus adhering the gel to the tissue. In embodiments, the reactive members may be either a dipolarophile or a 1,3 dipolar compound depending on which complement is applied to the target tissue or the medical gel. For example, if a dipolarphile is located on the gel, the 1,3 dipolar compound will be located on the tissue. If a dipolarphile is located on the tissue, the 1,3 dipolar compound will be located on the gel. In embodiments, the Diels-Alder members of a specific binding pair may be either a diene and a dienophile depending on which complement is applied to the target tissue or the medical gel. For example, if a diene is located on the gel, the dienophile can be located on the tissue. If a diene is located on the tissue, the dienophile can be located on the gel. In embodiments, the thiol-ene members of a specific binding pair may be either a thiol and an alkene depending on which complement is applied to the target tissue or the gel. For example, if a thiol is located on the gel, the alkene can be located on the tissue. If a thiol is located on the tissue, the alkene can be located on the gel.

The medical gel may be biocompatible and absorbable or biocompatible and non-absorbable. In one embodiment, the reactive members are attached directly to the polymeric backbone of the gel. In another embodiment, the reactive members are attached to the polymeric backbone via a cross-linker. Cross-linkers are discussed below. Hydrogels can be formed, e.g., when an organic polymer, also referred to herein as precursor molecules which form the gel, which can be natural or synthetic, is set or at least partially solidified to create a three-dimensional open-lattice structure that entraps molecules of water or other solutions to form a gel. Hydrogels have an affinity for water and typically swell in water, but do not necessarily dissolve in water. Solidification can occur by aggregation, coagulation, hydrophobic interactions, cross-linking, or similar means. In certain embodiments, hydrogels are formed by polymerization and crosslinking of a hydrophilic monomer in an aqueous solution to cause the solution to gel. In embodiments, the hydrogel is composed of 85% water, to which can be added any salt or adjuvant.

Hydrogels may be organic gels or inorganic gels. Organic gels from which the hydrogel of the invention can be selected include, by way of example and not by way of limitation, gels formed from polysaccharides and mucopolysaccharides including, but not limited to hyaluronic acid, dextran, heparin sulfate, chondroitin sulfate, agar, starch, and alginate; proteins, including but not limited to, fibronectin, gelatin, collagen, fibrin, chitosan, chitin, pectins, albumin, ovalbumin, and polyamino acids; collagen-hydroxyethyl-methacrylate (HEMA); polyphosphazines; polyphosphoesters; polyethylene glycol; polyethylene oxide; polyvinyl alcohol; polyvinylpyrrolidone; polyethyloxazoline; polyethylene oxide-co-polypropyleneoxide block copolymers; PGA-PEG-PGA block copolymers; PGA-PEG diblock copolymers; acrylates, including but not limited to diacrylates, oligoacrylates, methacrylates, dimethacrylates and oligomethacrylates; PEG-oligoglycolylacrylates; polyacrylonitriles (PAN); carboxy alkyl celluloses, including but not limited to carboxymethyl cellulose; partially oxidized cellulose; biodegradable polymers including but not limited to polymers and oligomers of glycolide, lactide, polyesters of α-hydroxy acids, including lactic acid and glycolic acid, such as the poly(α-hydroxy) acids including polyglycolic acid, poly-DL-lactic acid, poly-L-lactic acid, and terpolymers of DL-lactide and glycolide; ε-caprolactone and ε-caprolactone copolymerized with polyesters; polylactones and polycaprolactones including poly(ε-caprolactone), poly(δ-valerolactone) and poly(γ-butyrolactone); polyanhydrides; polyorthoesters; polydioxanone; and other biologically degradable polymers that are non-toxic or are present as metabolites in the body; as well as non-degradable polymers such as styrene and acrolein.

Collagen-hydroxyethyl-methacrylate (EMA) hydrogel polymer is commonly formed from a gelled and crosslinked hydrophilic monomer solution to form a three dimensional polymeric meshwork anchoring macromolecules. Crosslinking of the hydrophilic monomer solution can be accomplished by free radical polymerization of hydrophilic monomers, such as hydroxyethyl-methacrylate (HEMA). Hydrogel polymers formed by free radical polymerization of monomer solutions require crosslinking to form the three dimensional network to gel the aqueous solution. HEMA monomer solutions typically can be crosslinked to gel by dimethacrylate, although other crosslinking agents, such as ethylene glycol dimethacrylate or methylmethacrylate, can also be used during polymerization to modify the hydrogel. A wide variety of other hydrophilic monomers may also be suitable for purposes of the invention. Inorganic gels include, by way of example and not by way of limitation, silica, alumina, and ferric oxide.

Bulk and cellular hydrogels may be prepared by covalent cross linking or physical cross linking of the hydrogel molecules. Thus, covalent cross linking, also known as chemical cross linking, includes the use of multi-functional reactive chemical molecules such as aldehydes, maleic acid, dimethyl urea, di-isocyanates, boric acid, and the like, and also the use of ionizing radiation, ultraviolet light, and the like, while physical cross linking methods, also known as reversible cross linking, includes cross linking through crystallites, hydrogen bonding and complexing agents such as titanium, aluminum, manganese, and copper, to name a few. Physical cross linking through formation of crystallites in, e.g., polyvinyl alcohols, chitosan and the like, using, for example, partial freeze-drying, repeated freezing and thawing, low temperature crystallization, physical cross linking induced by the presence of aqueous solutions of organic compounds, salts, acids and bases and the like.

In the present application, the term "bioresorbable" and "bioabsorbable" are used interchangeably and are intended to mean the characteristic according to which an implant and/or a material is resorbed by the biological tissues and the surrounding fluids and disappears in vivo after a given period of time, that may vary, for example, from one day to several months, depending on the chemical nature of the implant and/or of the material. Non bioresorbable material—also called permanent material—is not substantially resorbed by tissues and surrounding fluids, after 2 years and more, keeping in particular most (e.g., >80%) of their mechanical properties after such a time. The term "biocompatible" is intended to mean the characteristic according to which an implant and/or a material is well integrated by the biological tissues and the surrounding fluids without inducing excessive inflammation reaction around the bulk of the material or due to its degradation. The material should avoid also the formation of a fibrous capsule which usually results in the delay of the cellular integration of a porous implant.

Many of the above described examples of polymers do not contain functional groups in their molecules. In embodiments, the reactive members are attached to the medical gel by surface modification techniques such as plasma treatment, silane coupling treatment and acid sensitization. Surface activation of the medical gel can be achieved by acid or base hydrolysis, treatment by means of cold plasma, by chemical reactions or electromagnetic radiations.

Hydrolysis can be conducted in the presence of an aqueous solution of a base or an acid to accelerate surface reaction, inasmuch as excessively long processes of activation can induce a reduction in molecular weight and thus in the mechanical properties of the material. Suitable bases for obtaining watery solutions suited to the aim are, for example, strong alkalis, such as LiOH, Ba(OH)$_2$, Mg(OH)$_2$, NaOH, KOH, Na$_2$CO$_3$, Ca(OH)$_2$ and the weak bases, such as for example NH$_4$ OH and the ammines such as methylamine, ethylamine, diethylamine and dimethylamine. Acids suitable for surface hydrolysis treatments can be chosen, for example, from among HCl, HClO$_3$, HClO$_4$, H$_2$ SO$_3$, H$_2$ SO$_4$, H$_3$ PO$_3$, H$_3$ PO$_4$, HI, HIO$_3$, HBr, lactic acid, glycolic acid. Surface activation by means of hydrolysis can be conducted at temperatures preferably comprised between 0 degrees Celsius and the material softening temperature.

Plasma treatment can be carried out both in the presence of a reactive gas, for example air, Ar, O$_2$ with the formation of surface activation of oxygenate type, such as —OH, —CHO, —COOH.

Surface treatment, whether hydrolytic or with plasma, can remain unaltered or can be followed by further chemical modifications to provide the first reactive groups on the bioabsorbable polymeric substrate. Thus, for example, the COONa groups generated by a base hydrolysis can be subsequently converted into COOH groups by treatment with strong mineral acids. Further, the surface freeing of alcoholic groups by means of a hydrolysis process can be followed by reaction by means of the addition of a compound provided with functional group or groups able to react with surface alcoholic groups, such as for example by means of the addition of an anhydride such as succinic anhydride, with the conversion of —OH groups into —O—CO—$CH_2$—$CH_2$—COOH groups. Suitable surface activation techniques are disclosed in U.S. Pat. No. 6,107,453, the entire disclosure of which is incorporated herein by this reference.

During manufacture of polymers, pendant functional groups can be incorporated into the polymer backbone by, e.g., copolymerization with functionalized monomer such as lactones, cyclic carbonates and morpholine-2,5-diones. The azido group, $N_3$ is a nucleophilic group that will exchange with other nucleophilic groups, e.g., —OH, —$NH_2$ and halogens (Br, Cl, or I). For example, 1,3-dipolar compounds may be conjugated to aliphatic polyesters, by copolymerizing, e.g., ε-caprolactone and α-chloro-ε-caprolactone and then substituting an azide group for the Cl atom. Polyesters can incorporate pendant dipolarophiles, e.g., propargyl groups, by copolymerization of ε-caprolactone and α-propargyl-δ-valerolactone. Copolymers of L-lactide containing propargyl groups may, e.g., be prepared by ring opening copolymerization of 5-methyl-5-propargyloxycarbonyl-1,3-dioxanone with L-lactide at a molar ratio of about 90:10 with $ZnEt_2$ as a catalyst. See, Shi et al., Biomaterials, 29 (2008) 1118-1126. Azide functionalized polystyrene is synthesized using atom transfer radical polymerization and subsequent modification with azidotrimethylsilane and tetrabutylammonium fluoride. See, Dirks, et al., Chem. Comm., (2005) 4172-4174. Azides may be incorporated onto methacrylates, e.g., 3 azidopropyl methacrylate which is copolymerized to a block copolymer. Diels-Alder functionalities and thiol-enc functionalities are likewise incorporated into polymers herein.

Biological tissue is provided with reactive members or complementary reactive members of a specific binding pair by conjugation to various components of tissue such as proteins, lipids, oligosaccharides, oligonucleotides, glycans, including glycosaminoglycans. In one embodiment, the reactive members or complementary reactive members are attached directly to components of the tissue. In another embodiment, the reactive members or complementary reactive members are attached to components of the tissue via a linker. In either case, situating the reactive members or complementary reactive members on the tissue can be accomplished by suspending the reactive members or complementary reactive members in a solution or suspension and applying the solution or suspension to the tissue such that the reactive member or complementary reactive members binds to a target. The solution or suspension may be poured, sprayed or painted onto the tissue, whereupon the reactive members are incorporated into the tissue.

1,3-Dipolar compounds can be incorporated into proteins, lipids, oligosaccharides, oligonucleotides and glycans using, e.g., metabolic machinery, covalent inhibitors and enzymatic transfers. For example, an azido group, $N_3$, can be applied at the N-terminus of proteins or peptides using azidoacetyl chloride. See, e.g., Haridas, et al., Tetrahedron Letters 48 (2007) 4719-4722. The azido group is a nucleophilic group that will exchange with other nucleophilic groups, e.g., —OH, —$NH_2$ and halogens (Br, Cl, or I). $NaN_3$ is an azidizing agent which is capable of aziding proteins by simply contacting the proteins with a 10 times molar excess of $NaN_3$. A process for C-terminal azidization is described in Cazalis, et al., Bioconjugate Chem., 15 (2004) 1005-1009. Incubation of cells with peracetylated N-azidoacetylmannosamine provides cell surface glycans with azido sialic acid. See, e.g., Codelli et al., J. Amer. Chem. Soc., 130 (34) 11486-11493 (2008). Azido-tagged lipids are described in Smith, et al., Bioconjugate Chem., 19 (9), 1855-1863 (2008). PEGylation is a commonly used technique for adding groups to to peptides and proteins and is suitable for use herein. For example, PEG may be covalently bound to amino acid residues via a reactive group. Reactive groups (as opposed to reactive members herein) are those to which an activated PEG molecule may be bound (e.g., a free amino or carboxyl group). For example, N-terminal amino acid residues and lysine (K) residues have a free amino group and C-terminal amino acid residues have a free carboxyl group. Sulfhydryl groups (e.g., as found on cysteine residues) may also be used as a reactive group for attaching PEG. In addition, enzyme-assisted methods for introducing activated groups (e.g., hydrazide, aldehyde, and aromatic-amino groups) specifically at the C-terminus of a polypeptide. Accordingly, PEG incorporating 1,3-dipolar compounds may be utilized herein Those skilled in the art can utilize any known process for coupling a 1,3-dipolar compound into proteins, lipids, oligosaccharides, oligonucleotides and glycans.

Dipolarophile functionalized proteins and peptides can be synthesized by linking at the N-terminus with, for example, an alkyne (e.g., 3 butynyl chloroformate), in connection with a tripeptide (GlyGlyArg). See, Dirks, et al., supra. A suitable tripeptide herein is the well-known cell adhesion sequence RGD. It should be understood that, as used herein, "proteins" is intended to encompass peptides and polypeptides. In one embodiment, thiols on cysteines are functionalized with alkyne bearing maleimide. Id. Providing a C-terminal dipolarophile can be accomplished, e.g., by coupling with propargylamine using a cross-linking agent such as N-hydroxysuccinimide/DCC. See, e.g., Haridas, et al. supra. Terminal alkynes can be installed using metabolic building blocks such as alkynoic acids. Lipids may be functionalized with alkynes. For example, alkyne modified fatty acids can be generated by reaction of terminal alkynyl-alkyl bromide with trimethyl phosphine to yield a 16-carbon alkynyl-dimethylphosphonate. See, e.g., Raghavan et al., Bioorg. Med. Chem. Lett., 18 (2008) 5982-5986. As above, PEGylation may be used for adding dipolarophile groups to peptides and proteins and is suitable for use herein. Diels-Alder functionalities and thiol-ene functionalities are likewise attached to proteins, lipids, oligosaccharides, oligonucleotides and glycans.

The reactive members or complementary reactive members may be also attached to biological tissue or the medical gel via a linker. In certain embodiments, the linker is or includes a ligand which bears a reactive member. The ligand binds to a desired target on the tissue and thus provides a vehicle for transporting and indirectly binding the reactive member or complementary reactive member to the tissue. The ligand herein is any molecule or combination of molecules which demonstrates an affinity for a target. Examples of ligands include nucleic acid probes, antibodies, hapten conjugates, and cell adhesion peptides such as RGD. The mechanisms involved in obtaining and using such ligands are well-known. In embodiments, reactive members or complementary reactive members are incorporated into saccharides or polysaccharides and metabolically incorporated into cells. See, e.g., Baskin et al., supra.

Antibodies that specifically recognize antigens are useful in accordance with one embodiment herein. Antibodies which are conjugated to a reactive member or complementary reactive members are utilized to bind to proteins located on tissue. Monoclonal or polyclonal antibodies are raised against an antigen which can be any component of biological tissue and then purified using conventional techniques. The term "antibody" is intended to include whole antibodies, e.g., of any isotype (IgG, IgA, IgM, IgE, etc.), and to include fragments thereof which are also specifically reactive with a vertebrate, e.g., mammalian, protein. Antibodies may be fragmented using conventional techniques and the fragments screened for utility in the same manner as for whole antibodies. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')$_2$, Fab', Fv, and single chain antibodies (scFv) containing a V[L] and/or V[H] domain joined by a peptide linker. The scFv's may be covalently or non-covalently linked to form antibodies having two or more binding sites. The present disclosure includes polyclonal, monoclonal or other purified preparations of antibodies and recombinant antibodies.

After purification, the ligands (e.g., antibodies, nucleic acid probes, hapten conjugates and cell adhesion peptides), are conjugated or linked to reactive members or complementary reactive members in the manners described above. In addition, reactive members or complementary reactive members can be linked to ligands by cross-linking procedures which, in accordance with the present invention, do not cause denaturing or misfolding of the ligands. The terms "linked" or "conjugated" as used herein are used interchangeably and are intended to include any or all of the mechanisms known in the art for coupling the reactive members or complementary reactive members to the ligand. For example, any chemical or enzymatic linkage known to those with skill in the art is contemplated including those which result from photoactivation and the like. Homofunctional and heterobifunctional cross linkers are all suitable. Reactive groups (distinguishable from reactive members or complementary reactive members herein) which can be cross-linked with a cross-linker include primary amines, sulfhydryls, carbonyls, carbohydrates and carboxylic acids.

Cross-linkers are conventionally available with varying lengths of spacer arms or bridges. Cross-linkers suitable for reacting with primary amines include homobifunctional cross-linkers such as imidoesters and N-hydroxysuccinimidyl (NHS) esters. Examples of imidoester cross-linkers include dimethyladipimidate, dimethylpimelimidate, and dimethylsuberimidate. Examples of NHS-ester cross-linkers include disuccinimidyl glutamate, disucciniminidyl suberate and bis(sulfosuccinimidyl) suberate. Accessible amine groups present on the N-termini of peptides react with NHS-esters to form amides. NHS-ester cross-linking reactions can be conducted in phosphate, bicarbonate/carbonate, HEPES and borate buffers. Other buffers can be used if they do not contain primary amines. The reaction of NHS-esters with primary amines should be conducted at a pH of between about 7 and about 9 and a temperature between about 4° C. and 30° C. for about 30 minutes to about 2 hours. The concentration of NHS-ester cross-linker can vary from about 0.1 to about 10 mM. NHS-esters are either hydrophilic or hydrophobic. Hydrophilic NHS-esters are reacted in aqueous solutions although DMSO may be included to achieve greater solubility. Hydrophobic NHS-esters are dissolved in a water miscible organic solvent and then added to the aqueous reaction mixture.

Sulfhydryl reactive cross-linkers include maleimides, alkyl halides, aryl halides and a-haloacyls which react with sulfhydryls to form thiol ether bonds and pyridyl disulfides which react with sulfhydryls to produce mixed disulfides. Sulfhydryl groups on peptides and proteins can be generated by techniques known to those with skill in the art, e.g., by reduction of disulfide bonds or addition by reaction with primary amines using 2-iminothiolane. Examples of maleimide cross-linkers include succinimidyl 4-{N-maleimidomethyl}cyclohexane-1-carboxylate and m-maleimidobenzoyl-N-hydroxysuccinimide ester. Examples of haloacetal cross-linkers include N-succinimidyl(4-iodoacetal)aminobenzoate and sulfosuccinimidyl(4-iodoacetal)aminobenzoate. Examples of pyridyl disulfide cross-linkers include 1,4-Di-[3'-2'-pyridyldithio(propionamido)butane] and N-succinimidyl-3-(2-pyridyldithio)-propionate.

Carboxyl groups are cross-linked to primary amines or hydrazides by using carbodimides which result in formation of amide or hydrazone bonds. In this manner, carboxy-termini of peptides or proteins can be linked. Examples of carbodiimide cross-linkers include 1-ethyl-3-(3-dimethylaminopropyl)-carbodiimide hydrochloride and N,$N^1$-dicyclohexylcarbodiimide. Arylazide cross-linkers become reactive when exposed to ultraviolet radiation and form aryl nitrene. Examples of arylazide cross-linkers include azidobenzoyl hydrazide and N-5-azido-2 nitrobenzoyloxysuccinimide. Glyoxal cross linkers target the guanidyl portion of arginine. An example of a glyoxal cross-linker is p-azidophenyl glyoxal monohydrate.

Heterobifunctional cross-linkers which possess two or more different reactive groups are suitable for use herein. Examples include cross-linkers which are amine-reactive at one end and sulfhydryl-reactive at the other end such as 4-succinimidyl-oxycarbonyl-a-(2-pyridyldithio)-toluene, N-succinimidyl-3-(2-pyridyldithio)-propionate and the maleimide cross-linkers discussed above.

Attachment of reactive members or complementary reactive members to the medical gel functionalizes the gel such that upon exposure to their complementary reactive members which are situated on tissue, they are activated and form a covalent bond, thus adhering the gel to the tissue. In one embodiment, a linker between the product of the reactive members or complementary reactive members and the biological tissue is degradable by, e.g., hydrolysis or enzymatic action. In this manner, the medical gel can be removable after a period of time. The degradable linkage may be chelates or chemically or enzymatically hydrolyzable or absorbable. Illustrative chemically hydrolyzable degradable linkages include polymers, copolymers and oligomers of glycolide, dl-lactide, 1-lactide, caprolactone, dioxanone, and tritnethylene carbonate. Illustrative enzymatically hydrolyzable biodegradable linkages include peptidic linkages cleavable by metalloproteinases and collagenases and chitosan cleavable by lysozyme. Additional illustrative degradable linkages include polymers and copolymers of poly(hydroxy acid)s, poly(orthocarbonate)s, poly(anhydride)s, poly(lactone)s, poly (amino acid)s, poly(carbonate)s, poly(saccharide)s and poly (phosphonate)s. In certain embodiments, the degradable linkage may contain ester linkages. Some non-limiting examples include esters of succinic acid, glutaric acid, propionic acid, adipic acid, or amino acids, as well as carboxymethyl esters.

The ligand solution and gel can be sterilized by any known method, e.g., irradiation, ethylene oxide, filtration in sterile conditions on a 0.22 um filter and the like.

Medical gels herein may be used in a variety of applications. In one embodiment, the gel is an uncured liquid, functionalized with a plurality of reactive members of a binding pair, which is applied and cured as a layer on surfaces of internal organs or tissues which were pretreated with the complementary reactive member as described above. The target tissue is pretreated by spraying, painting or pouring a solution or suspension containing the complementary reactive members of a binding pair on to the tissue. Ligands associated with the reactive members or complementary reactive members bind to their predetermined targets on the tissue, thereby anchoring the reactive members or complementary reactive members on the tissue. The uncured functionalized liquid gel is sprayed over, e.g., a defect on the tissue where it cures while simultaneously, the reactive members and complementary reactive members of the specific binding pair react specifically together to form covalent bonds, providing adhesion between the tissue and the curing or cured gel. In another embodiment, the functionalized gel is cured prior to application to pretreated tissue and then draped over or otherwise contacted with the target or defect to allow the covalent bond forming reaction to occur with consequent covalent bonding and adherence. In certain embodiments, two opposing tissue surfaces are pretreated and functionalized, and functionalized gel added to form bonds to both opposing surfaces.

Some applications include using the medical gel composition to bind tissue together either as an adjunct to or as a replacement of sutures, staples, tapes and/or bandages. In another application, the present gels may be used to prevent post-surgical adhesions. In this application, the gel, functionalized with a reactive member of a binding pair, is applied and cured as a layer on surfaces of internal organs or tissues which were pretreated with a complementary reactive member of the binding pair as described above in order to prevent the formation of adhesions at a surgical site as the site heals. In another application, the functionalized gel may be used to attach pretreated skin grafts and to position pretreated tissue flaps or free flaps during reconstructive surgery. In still another application, the functionalized gel may be used to close pretreated gingival flaps in periodontal surgery. Additional applications include sealing tissues to prevent or control blood or other fluid leaks at suture or staple lines as well as to prevent or control air leaks in the pulmonary system.

In addition, functionalized medical gels herein can be used as bulking agents, e.g., they can be injected via a syringe and needle or other generally accepted means directly into a specific area wherever a bulking agent is desired, i.e., a pretreated soft tissue deformity such as that seen with areas of muscle atrophy due to congenital or acquired diseases or secondary to trauma, burns, and the like. An example of this would be the injection of a medical gel herein in the upper torso of a patient with muscular atrophy secondary to nerve damage. A medical gel herein can also be injected as a bulking agent for hard tissue defects, such as bone or cartilage defects, either congenital or acquired disease states, or secondary to trauma, burns, or the like. An example of this would be an injection into the area surrounding the skull where a bony deformity exists secondary to trauma. The injection in these instances can be made directly into the needed area with the use of a needle and syringe under local or general anesthesia.

A medical gel could also be injected percutaneously by direct palpation, such as by placing a needle inside a pretreated vas deferens and occluding the same with the injected functionalized bulking medical gel, thus rendering the patient infertile. The gel could also be injected through a catheter or needle with fluoroscopic, sonographic, computed tomography, magnetic resonance imaging or other type of radiologic guidance. This would allow for placement or injection of the pretreatment formulation and subsequent functionalized medical gel either by vascular access or percutaneous access to specific organs or other tissue regions in the body, wherever a bulking agent would be required.

Techniques of tissue engineering employing functionalized medical gel scaffolds can be used to create alternatives to prosthetic materials currently used in craniomaxillofacial surgery, as well as formation of organ equivalents to replaced diseased, defective, or injured tissues. Medical gels herein can be malleable and used to encapsulate cells. To form a hydrogel containing the cells, a functionalized polymer solution is mixed with the cells to be implanted to form a suspension. Then, in one embodiment, the target site is pretreated with complementary members of a specific binding pair and the functionalized polymers in suspension are injected directly into a patient prior to crosslinking of the polymer to form the hydrogel containing the cells. The hydrogel cures over a short period of time while simultaneously binding to the pretreated area through covalent bond formation. In another embodiment, the functionalized gel is injected or poured into a mold, where it crosslinks to form a semi-solid hydrogel of the desired anatomical shape having cells dispersed therein which then may be implanted in a pretreated target area in a patient. The hydrogel may be produced, for example, by cross-linking a polysaccharide polymer by exposure to a monovalent cation. Other polymers capable of forming functionalized hydrogels as described above may be used as disclosed herein. In the embodiments where the functionalized polymer is crosslinked by contact with a crosslinking agent, the strength of the crosslink may be increased or reduced by adjusting the concentration of the polymer and/or crosslinking agent.

Further, combinations in accordance with this disclosure, e.g., functionalized medical gel having reactive members of a specific binding pair and functionalized pretreatment formulation containing complementary members of the specific binding pair, could be injected through a laparoscope or thoracoscope to any intraperitoneal or extraperitoneal or thoracic organ. For example, the functionalized pretreatment formulation and functionalized gel could be injected in the region of the gastroesophageal junction for the correcting of gastroesophageal reflux. This could be performed either with a thoracoscope injecting the substances in the esophageal portion of the gastroesophageal region, or via a laparoscope by injecting the substances in the gastric portion of the gastroesophageal region, or by a combined approach.

A kit for a functionalized adhesive herein includes a medical gel which has a plurality of reactive members of a specific binding pair adapted to be attached to a surface of the gel and an applicator adapted to contain a solution or suspension of complementary reactive members of the specific binding pair, the complementary reactive members having a functionality that will adhere them to biological tissue upon contact. The kit may optionally include a container which contains a catalyst for causing the reactive members of a specific binding pair to bind with the complementary reactive members of the specific binding pair. The catalyst may be a solution of metal such as copper. In embodiments, the kit contains a microwave or ultraviolet radiation generator.

It should be understood that variations can be made to the above embodiments that are with the purview of ordinary skill in the art. For example, other click chemistry reactions are suitable for use herein, e.g., staudinger reaction of phosphines with alkyl azides. Accordingly, those skilled in the art can envision modifications which are included within the scope of the claimed invention that are not expressly set forth herein.

What is claimed is:

1. A method for adhering a medical gel to biological tissue comprising:
   providing a medical gel having a plurality of reactive members of a specific binding pair attached to the medical gel; and
   providing tissue with a plurality of complementary reactive members of the specific binding pair, wherein the complementary reactive members are conjugated to ligands which bind to a receptor to link the complementary reactive members to the tissue via a ligand-receptor linkage and upon contact of the reactive members of the medical gel with the complimentary reactive members linked to the tissue, covalent bonds are formed via click chemistry between the reactive members and the complementary reactive members, adhering the medical gel to the tissue.

2. The method for adhering a medical gel to biological tissue according to claim 1 wherein the members of the specific binding pair bind to one another via a reaction selected from the group consisting of Huisgen cycloaddition reaction, a Diels-Alder reaction and a thiol-ene reaction.

3. The method for adhering a medical gel to biological tissue according to claim 2 wherein the members of the specific binding pair are alkynes and azides.

4. The method for adhering a medical gel to biological tissue according to claim 3 wherein the reactive member is an alkyne and the complementary reactive member is an azide.

5. The method for adhering a medical gel to biological tissue according to claim 3 wherein the reactive members is an azide and the complementary reactive member is an alkyne.

6. The method for adhering a medical gel to biological tissue according to claim 2 wherein the reaction is catalyzed by metal to activate an alkyne and an azide for [3+2] cycloaddition.

7. The method for adhering a medical gel to biological tissue according to claim 2 wherein the tissue is provided with complementary reactive members of the specific binding pair by applying a mixture or an aerosol containing the complementary reactive members to the tissue.

8. The method for adhering medical gel to biological tissue according to claim 7 wherein the complementary reactive members are conjugated to a ligand selected from the group consisting of antibody, Fab, F(ab')$_2$, Fv, single chain antibody (SCA) and single complementary-determining region (CDR).

9. The method for adhering a medical gel to biological tissue according to claim 7 wherein the ligand binds to a receptor selected from the group consisting of peptides, oligosaccharides, oligonucleotides and lipids.

10. The method for adhering a medical gel to biological tissue according to claim 1 wherein the medical gel is made of a polymer selected from the group consisting of polysaccharides, mucopolysaccharides, polyaminoacids, proteins, collagen-hydroxyethyl-methacrylate (HEMA), polyphosphazines, polyphosphoesters, polyethylene glycol, polyethylene oxide, polyvinyl alcohol, polyvinylpyrrolidone, polyethyloxazoline, polyethylene oxide-co-polypropyleneoxide block copolymers, PGA-PEG-PGA block copolymers, PGA-PEG diblock copolymers, acrylates, PEG-oligoglycolylacrylates, polyacrylonitriles (PAN), carboxy alkyl celluloses, poly($\alpha$-hydroxy) acids, polylactones, polycaprolactones, polyanhydrides, polyorthoesters, polydioxanone, styrene, acrolein and copolymers, block copolymers, homoploymers, blends and combinations thereof.

11. The method for adhering a medical gel to biological tissue according to claim 10 wherein the mucopolysachamides are selected from the group consisting of hyaluronic acid, dextran, heparin sulfate, chondroitin sulfate, heparin, agar, starch, and alginate; the proteins are selected from the group consisting of fibronectin, gelatin, collagen, fibrin, pectins, albumin, ovalbumin, and polyamino acids; the acrylates are selected from the group consisting of diacrylates, oligoacrylates, methacrylates, dimethacrylates and oligomethoacrylates; the carboxy alkyl celluloses are selected from the group consisting of carboxymethyl cellulose and partially oxidized cellulose; poly($\alpha$-hydroxy) acids selected from the group consisting of polyglycolic acid, poly-DL-lactic, poly-L-lactic acid, and terpolymers of DL-lactide and glycolide; and
   polylactones selected from the group consisting of poly($\epsilon$-caprolactone), poly($\delta$-valerolactone) and poly(y-butyrolactone), $\epsilon$-caprolactone copolymerized with polyesters.

* * * * *